US00PP36405P2

(12) United States Plant Patent
Koot

(10) Patent No.: US PP36,405 P2
(45) Date of Patent: Jan. 21, 2025

(54) ***SCAEVOLA* PLANT NAMED 'Doscascacappur'**

(50) Latin Name: *Scaevola aemula*
Varietal Denomination: Doscascacappur

(71) Applicant: DUMMEN GROUP B.V., De Lier (NL)

(72) Inventor: Arjan Koot, Oeffelt (NL)

(73) Assignee: Dümmen Group B.V., De Lier (NL)

( * ) Notice: Subject to any disclaimer, the term of this patent is extended or adjusted under 35 U.S.C. 154(b) by 0 days.

(21) Appl. No.: 18/663,019

(22) Filed: May 13, 2024

(51) Int. Cl.
*A01H 5/02* (2018.01)
*A01H 6/00* (2018.01)

(52) U.S. Cl.
USPC ..... Plt./363

(58) Field of Classification Search
USPC ..... Plt./363
See application file for complete search history.

*Primary Examiner* — Susan McCormick Ewoldt
(74) *Attorney, Agent, or Firm* — C. Anne Whealy

(57) ABSTRACT

A new and distinct cultivar of *Scaevola* plant named 'Doscascacappur', characterized by its compact, upright to outwardly spreading and mounding plant habit; freely branching habit; early and freely flowering habit; long flowering period; flowers that are bright purple in color; and good container and garden performance.

1 Drawing Sheet

Botanical designation: *Scaevola aemula.*
Cultivar denomination: 'DOSCASCACAPPUR'.

STATEMENT REGARDING PRIOR DISCLOSURES BY INVENTOR and APPLICANT/ASSIGNEE

The Inventor and Applicant/Assignee assert that no sales, offers for sale or public distribution of the instant plant occurred more than one year prior to the effective filing date of this application. Any information about the claimed plant would have been obtained from a direct or indirect disclosure from the Inventor and/or Applicant/Assignee. Inventor and Applicant/Assignee claim a prior art exception under 35 U.S.C. 102 (b) (1) for disclosures and/or sales prior to the filing date but less than one year prior to the effective filing date.

BACKGROUND OF THE INVENTION

The present invention relates to a new and distinct cultivar of *Scaevola* plant, botanically known as *Scaevola aemula* and hereinafter referred to by the name 'Doscascacappur'.

The new *Scaevola* plant a product of a planned breeding program conducted by the Inventor in Rheinberg, Germany. The objective of the breeding program is to create new freely-branching, mounding and early-flowering *Scaevola* plants with numerous attractive flowers.

The new *Scaevola* plant originated from a cross-pollination in Rheinberg, Germany in July 2020 of a proprietary selection of *Scaevola aemula* identified by the code number CC20-X0001, not patented, as the female, or seed, parent with a proprietary selection of *Scaevola aemula* identified as code number CC19-K0027, not patented, as the male, or pollen, parents. The new *Scaevola* plant was discovered and selected by the Inventor as a single flowering plant from within the progeny of the stated cross-pollination in a controlled greenhouse environment in Rheinberg, Germany in May 2021.

Asexual reproduction of the new *Scaevola* plant by vegetative tip cuttings in a controlled greenhouse environment in Rheinberg, Germany since May 2021 has shown that the unique features of this new *Scaevola* plant are stable and reproduced true to type in successive generations.

SUMMARY OF THE INVENTION

Plants of the new *Scaevola* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Doscascacappur'. These characteristics in combination distinguish 'Doscascacappur' as a new and distinct *Scaevola* plant:

1. Compact, upright to outwardly spreading and mounding plant habit.
2. Freely branching habit.
3. Early and freely flowering habit.
4. Long flowering period.
5. Flowers that are bright purple in color.
6. Good container and garden performance.

Plants of the new *Scaevola* can be compared to plants of the female parent selection. Plants of the new *Scaevola* differ primarily from plants of the female parent selection in the following characteristics:

1. Plants of the new *Scaevola* are more compact than plants of the female parent selection.
2. Plants of the new *Scaevola* are denser than and not as open as plants of the female parent selection.
3. Plants of the new *Scaevola* are more freely branching than plants of the female parent selection.

Plants of the new *Scaevola* can be compared to plants of the male parent selection. Plants of the new *Scaevola* differ primarily from plants of the male parent selection in the following characteristics:

1. Plants of the new *Scaevola* are more compact than plants of the male parent selection.
2. Plants of the new *Scaevola* are denser than and not as open as plants of the male parent selection.
3. Plants of the new *Scaevola* are more uniformly mounding than plants of the male parent selection.

Plants of the new *Scaevola* can be compared to plants of the *Scaevola aemula* 'Purple Haze', not patented. In side-by-side comparisons, plants of the new *Scaevola* differ from plants of the 'Purple Haze' in the following characteristics:

1. Plants of the new *Scaevola* are more compact than plants of 'Purple Haze'.
2. Plants of the new *Scaevola* are denser than and not as open as plants of 'Purple Haze'.
3. Plants of the new *Scaevola* are more mounding than and not as upright as plants of 'Purple Haze'.
4. Plants of the new *Scaevola* have larger flowers than plants of 'Purple Haze'.

BRIEF DESCRIPTION OF THE PHOTOGRAPH

The accompanying colored photograph illustrates the overall appearance of the new *Scaevola* plant showing the colors as true as it is reasonably possible to obtain in colored reproductions of this type. Colors in the photograph may differ slightly from the color values cited in the detailed botanical description which accurately describe the colors of the new *Scaevola* plant.

The photograph is a side perspective view of a typical flowering plant of 'Doscascacappur'.

DETAILED BOTANICAL DESCRIPTION

The aforementioned photograph and following observations and measurements describe plants grown during the summer in 22-cm containers in a glass-covered greenhouse in Rheinberg, Germany and under cultural practices typical of commercial *Scaevola* production. During the production of the plants, day and night temperatures averaged 18° C. and light levels averaged 4,500 lux. Plants were pinched one time about three weeks after planting. Plants were twelve weeks old when the photograph was taken and 25 weeks old when the description was taken. In the following description, color references are made to The Royal Horticultural Society Colour Chart, Fifth Edition, except where general terms of ordinary dictionary significance are used.

Botanical classification: *Scaevola aemula* 'Doscascacappur'.

Parentage:

*Female, or seed, parent*.—Proprietary selection of *Scaevola aemula* identified as code number CC20-X0001, not patented.

*Male or pollen parent*.—Proprietary selection of *Scaevola aemula* identified as code number CC19-K0027, not patented.

Propagation:

*Type*.—By vegetative tip cuttings.

*Time to initiate roots, summer*.—About five days at temperatures about 20° C.

*Time to initiate roots, winter*.—About seven days at temperatures about 20° C.

*Time to develop roots, summer*.—About three weeks at temperatures about 20° C.

*Time to develop roots, winter*.—About four weeks at temperatures about 20° C.

*Root description*.—Fine, fibrous; typically close to 162C in color, actual color of the roots is dependent on substrate composition, water quality, fertilizer type and formulation, substrate temperature and physiological age of roots.

*Rooting habit*.—Freely branching; medium density.

Plant description:

*Plant and growth habit*.—Compact, upright to outwardly spreading and mounding plant habit; moderately vigorous growth habit and moderate growth rate.

*Branching habit*.—Freely branching habit with about five to seven primary lateral branches each with about four to six secondary lateral branches developing per plant; pinching enhances branching potential.

*Plant height*.—About 23.5 cm.

*Plant diameter* (*area of spread*).—About 52 cm.

Lateral branch description:

*Length*.—About 28 cm.

*Diameter*.—About 5 mm.

*Internode length*.—About 4.3 cm.

*Aspect*.—Mostly outwardly, spreading.

*Texture and luster*.—Smooth, glabrous; matte.

*Color, developing*.—Close to 144B.

*Color, developed*.—Close to N137D; at the internodes, close to 137A.

Leaf description:

*Arrangement*.—Alternate, simple.

*Length*.—About 4 cm.

*Width*.—About 1.2 cm.

*Shape*.—Spatulate.

*Apex*.—Obtuse.

Base.—Attenuate.

*Margin*.—Dentate; incisions relatively shallow in depth and divergent.

*Texture and luster, upper and lower surfaces*.—Smooth, glabrous; matte.

*Venation pattern*.—Pinnate.

*Color*.—Developing leaves, upper surface: Close to N137A. Developing leaves, lower surface: Close to 146A. Fully expanded leaves, upper surface: Close to N137D; venation, close to 137A. Fully expanded leaves, lower surface: Close to 146A to 146B; venation, close to 137A.

*Petioles*.—Length: About 3 mm. Diameter: About 4 mm. Strength: Moderately strong. Texture and luster: Smooth, glabrous; semi-glossy. Color, upper and lower surfaces: Close to 144A.

Flower description:

*Flower type and shape*.—Zygomorphic, semi-circular, fan-shaped flowers with five petals fused at the base to form a tubular flower throat; flower throat open along the upper surface exposing the reproductive organs.

*Flower arrangement and quantity*.—Solitary sessile flowers arising from upper leaf axils; flowers mostly horizontal; freely flowering habit with typically about 875 flowers per plant developing during the flowering season.

*Flowering time*.—Early flowering habit, plants begin flowering after about six weeks after planting; long flower period, plants flower continuously from spring into the late summer in Northern Europe.

*Flower longevity*.—Flowers typically last about five to seven days on the plant; flowers not persistent.

*Fragrance*.—None detected.

*Flower buds*.—Length: About 1.5 cm. Diameter: About 3.2 mm. Shape: Ensiform. Texture and luster: Smooth, glabrous; matte. Color: Close to 145B and 84D.

*Flowers*.—Diameter: About 1.2 cm by 2.4 cm. Depth: About 2.4 cm. Throat diameter: About 3.2 mm. Tube length: About 9 mm. Tube diameter: About 2.2 mm.

*Petals*.—Quantity per flower: Five, fused at base. Length, beyond tube: About 9 mm. Width, beyond tube: About 4 mm. Shape: Narrowly elliptic. Apex: Acute. Margin: Entire; not undulate. Texture and luster, upper and lower surfaces: Smooth, glabrous; matte. Texture, throat: Smooth, glabrous. Texture, tube: Pubescent; rough. Color: When opening, upper surface: Close to N87B. When opening, lower surface: Close to N87A and 84D. Fully opened, upper surface: Close to N87A; venation, close to 86A; color does not change with subsequent development. Fully opened, lower surface: Close to N87B and N87C to N87D; venation, close to 83A; color becoming closer to N87B and 86C to 86B with subsequent development. Throat: Distally, close to NN155A and proximally, close to 145B; venation, close to 86A. Tube: Close to 151C; venation, close to 86A and NN144C to NN144D.

*Sepals*.—Quantity per flower: Three, one large and two smaller sepals fused at the base. Length, larger sepal: About 9 mm. Length, smaller sepals: About 4 mm. Width, larger sepal: About 3.3 mm. Width, smaller sepals: About 0.8 mm. Shape, all sepals: Lanceolate. Apex, all sepals: Acute. Margin, all sepals: Entire. Texture and luster, all sepals, upper and lower surfaces: Pubescent, rough; matte. Color, upper surface: Close to N137C. Color, lower surface: Close to 138A.

*Reproductive organs*.—Androecium: Stamen quantity per flower: Five or six. Filament length: About 2.8 mm. Filament color: Close to 161D. Anther size: About 0.3 mm by 1.7 mm. Anther shape: Ellipsoidal. Anther color: Close to 166B. Pollen: Sparse. Pollen color: Close to 4C. Gynoecium: Pistil quantity per flower: One. Pistil length: About 1.1 cm. Style length: About 7.5 mm. Style color: Close to N79B and 157B. Stigma diameter: About 2 mm. Stigma shape: Oblate. Stigma color: Close to 155B and 155C. Ovary color: Close to 144B.

*Fruits/seeds*.—To date, fruit and seed development has not been observed on plants of the new *Scaevola*.

Garden performance: Plants of the new *Scaevola* have been observed to have good garden performance and to tolerate rain, wind and temperatures ranging from about 3° C. to about 40° C. and to be suitable for USDA Hardiness Zone 11.

Pathogen & pest resistance: To date, plants of the new *Scaevola* have not been shown to be resistant to pathogens and pests common to *Scaevola* plants.

It is claimed:

1. A new and distinct *Scaevola* plant named 'Doscascacappur' as illustrated and described herein.

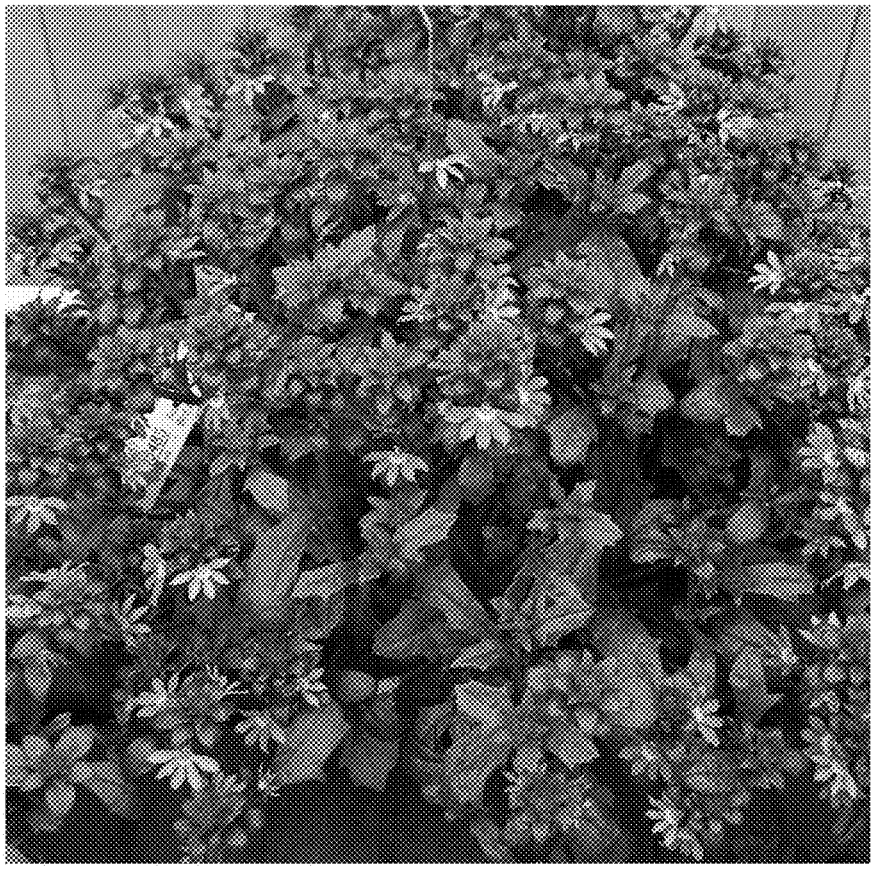

* * * * *